(12) United States Patent
WasDyke

(10) Patent No.: US 7,534,251 B2
(45) Date of Patent: May 19, 2009

(54) RETRIEVABLE IVC FILTER

(75) Inventor: Joel M. WasDyke, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 741 days.

(21) Appl. No.: 10/361,983

(22) Filed: Feb. 11, 2003

(65) Prior Publication Data

US 2004/0158274 A1    Aug. 12, 2004

(51) Int. Cl.
*A61M 29/00* (2006.01)
(52) U.S. Cl. ................................... 606/200
(58) Field of Classification Search ............... 606/113, 606/114, 127, 151, 157, 159, 200
See application file for complete search history.

(56) References Cited

U.S. PATENT DOCUMENTS

| | | | |
|---|---|---|---|
| 4,425,908 A | 1/1984 | Simon | |
| 4,688,553 A | 8/1987 | Metals | |
| 4,781,177 A | 11/1988 | Lebigot | |
| 4,817,600 A | 4/1989 | Herms et al. | |
| 4,957,501 A | 9/1990 | Lahille et al. | |
| 4,969,891 A | 11/1990 | Gewertz | |
| 5,059,205 A | 10/1991 | El-Nounou et al. | |
| 5,071,407 A | 12/1991 | Termin et al. | |
| 5,108,418 A | 4/1992 | Lefebvre | |
| 5,133,733 A | 7/1992 | Rasmussen et al. | |
| 5,152,777 A | 10/1992 | Goldberg et al. | |
| 5,160,342 A | 11/1992 | Reger et al. | |
| 5,221,261 A | 6/1993 | Termin et al. | |
| 5,300,086 A | 4/1994 | Gory et al. | |
| 5,329,942 A | 7/1994 | Gunther et al. | |
| 5,344,427 A | 9/1994 | Cottenceau et al. | |
| 5,370,657 A | 12/1994 | Irie | |
| 5,375,612 A * | 12/1994 | Cottenceau et al. | ......... 606/200 |
| 5,549,626 A | 8/1996 | Miller et al. | |
| 5,827,324 A | 10/1998 | Cassell et al. | |
| 5,836,969 A | 11/1998 | Kim et al. | |
| 5,893,869 A | 4/1999 | Barnhart et al. | |
| 6,126,673 A | 10/2000 | Kim et al. | |
| 6,168,579 B1 | 1/2001 | Tsugita | |
| 6,171,328 B1 | 1/2001 | Addis | |
| 6,179,859 B1 | 1/2001 | Bates et al. | |
| 6,231,581 B1 * | 5/2001 | Shank et al. | ................ 606/200 |
| 6,342,063 B1 | 1/2002 | DeVries et al. | |
| 6,391,045 B1 | 5/2002 | Kim et al. | |
| 6,436,120 B1 | 8/2002 | Meglin | |
| 6,436,121 B1 | 8/2002 | Blom | |

(Continued)

FOREIGN PATENT DOCUMENTS

WO    WO 01/60442 A1    8/2001

(Continued)

*Primary Examiner*—Kevin T Truong
(74) *Attorney, Agent, or Firm*—Crompton Seager & Tufte LLC

(57) ABSTRACT

Retrievable vena cava filters for filtering blood clots within a vessel are disclosed. A retrievable vena cava filter in accordance with an exemplary embodiment of the present invention may include a plurality of elongated filter legs each having a hook portion configured to engage the vessel wall, and an expandable member releasably connected to the filter. In certain embodiments, the expandable member may comprise a bendable member and several tubular members, or a coiled wire.

14 Claims, 8 Drawing Sheets

U.S. PATENT DOCUMENTS

| | | |
|---|---|---|
| 6,443,971 B1 | 9/2002 | Boylan et al. |
| 6,482,222 B1 | 11/2002 | Bruckheimer et al. |
| 6,485,501 B1 | 11/2002 | Green |
| 6,491,698 B1 | 12/2002 | Bates et al. |
| 6,511,496 B1 | 1/2003 | Huter et al. |
| 6,511,503 B1 | 1/2003 | Burkett et al. |
| 6,540,767 B1 * | 4/2003 | Walak et al. ............ 606/200 |
| 6,582,447 B1 * | 6/2003 | Patel et al. ............ 606/200 |

FOREIGN PATENT DOCUMENTS

| | | |
|---|---|---|
| WO | WO 01/62184 A2 | 8/2001 |
| WO | WO 02/069845 A2 | 9/2002 |
| WO | WO 02/089869 A2 | 11/2004 |

* cited by examiner

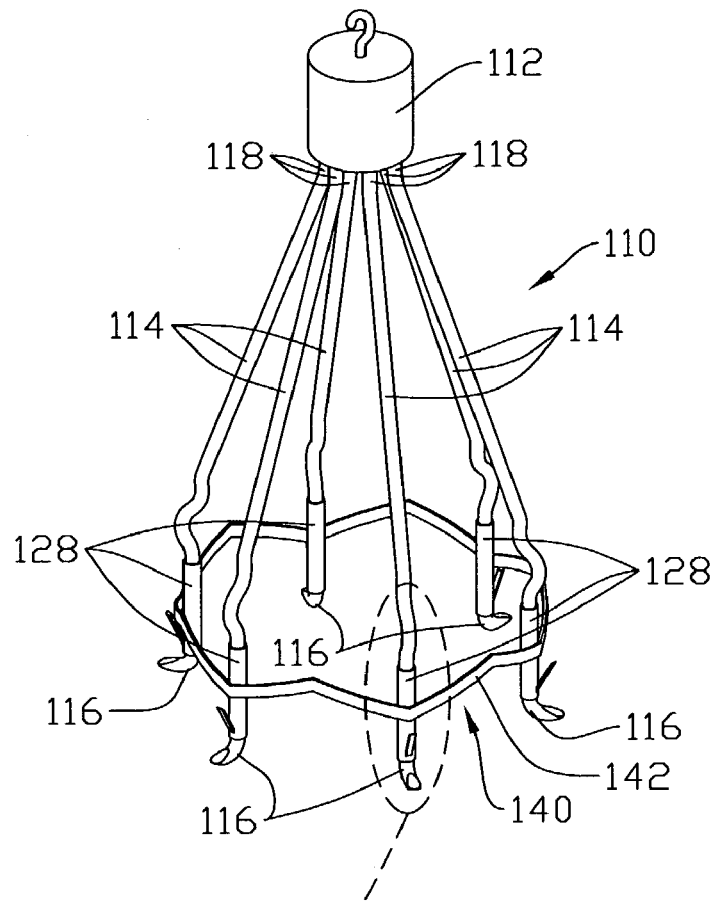
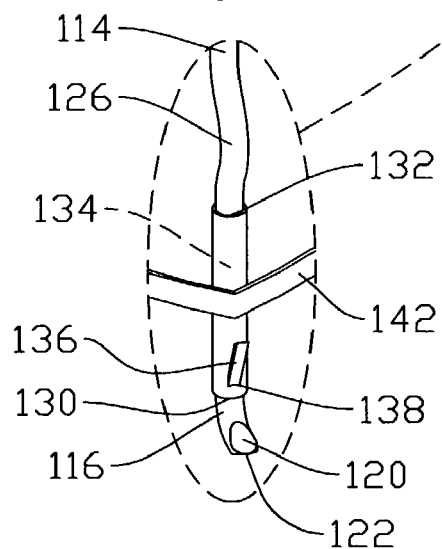
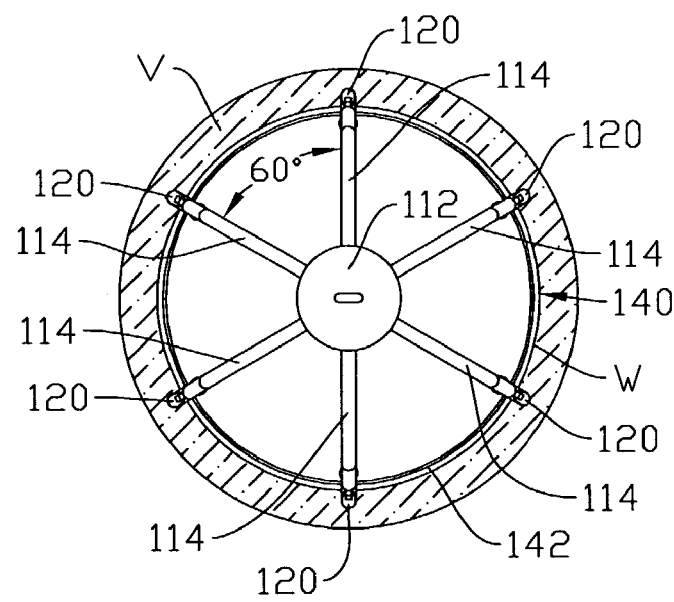

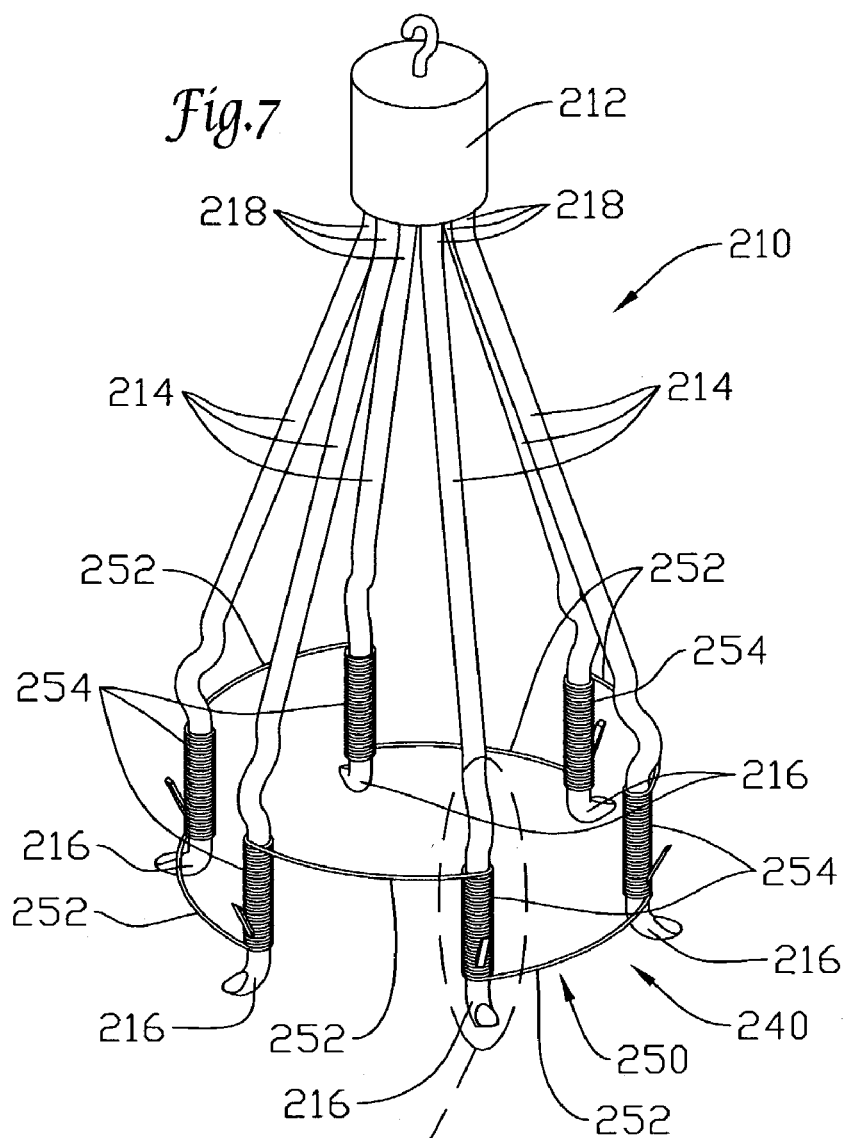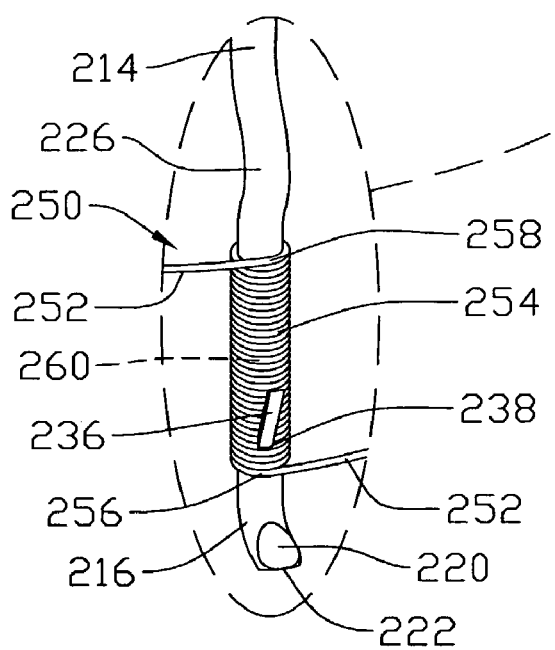

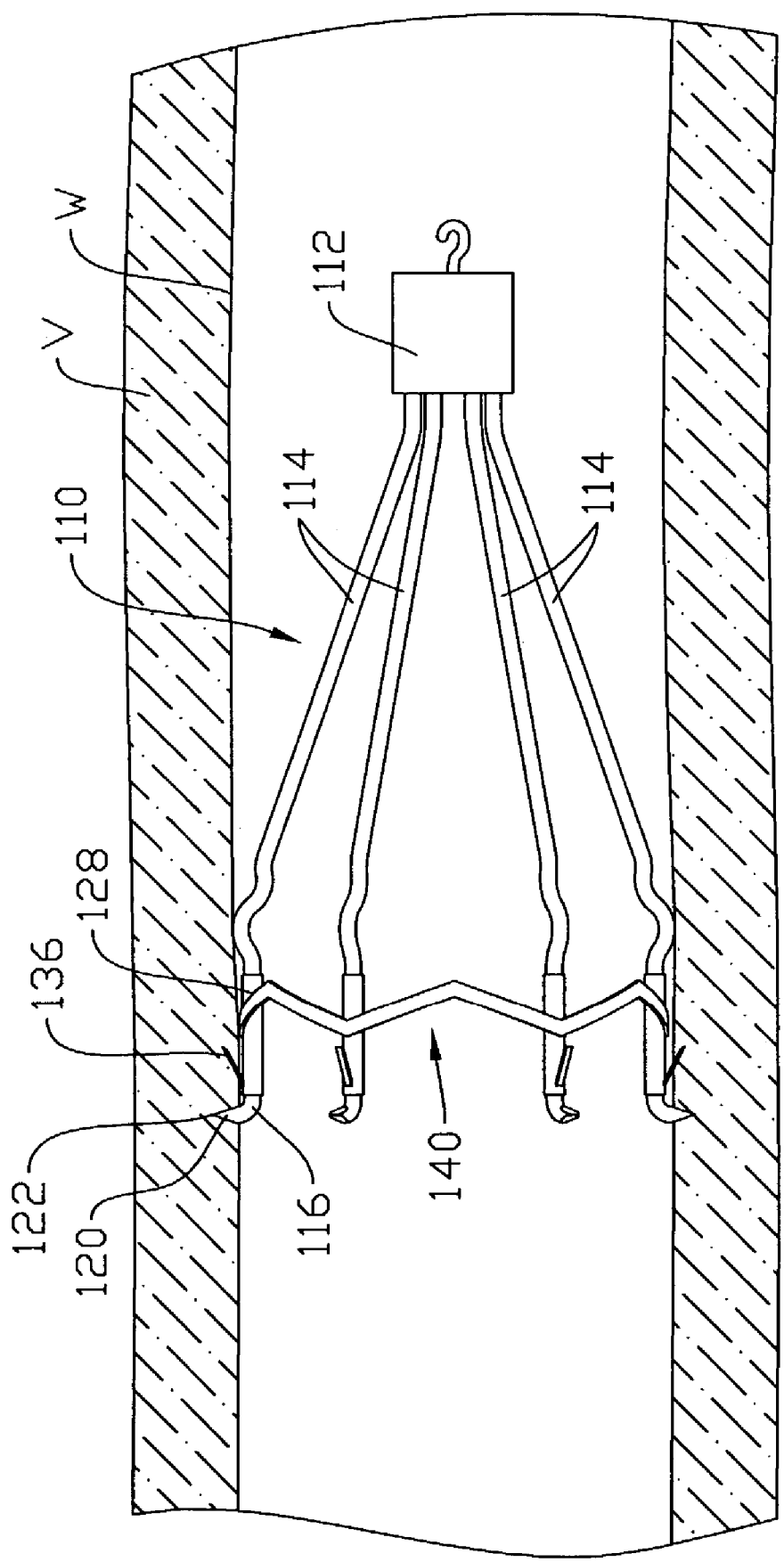

RETRIEVABLE IVC FILTER

FIELD OF THE INVENTION

The present invention relates to devices for filtering blood clots within a vessel. More specifically, the present invention pertains to retrievable intravascular filter devices implantable within the vena cava.

BACKGROUND OF THE INVENTION

Vena cava filters are utilized in conjunction with anti-coagulants and thrombolytic agents to prevent pulmonary embolism and other vascular diseases from occurring within the body. These devices are generally implanted within a vessel such as the inferior vena cava, and function by capturing blood clots (emboli) contained in the blood stream before they can reach the lungs and cause permanent damage to the patient.

To trap emboli, many conventional vena cava filters employ several independent filter legs that can be expanded in the vessel to form a conical-shaped filtering surface on which emboli can be collected. To enable ligation of the filter within the body, a hook, barb or other piercing means on the each filter leg can be used to anchor the filter along the cava wall. After a period of time within the body, tissue on the vessel wall begins to form about the ends of the filter legs, making removal of the device more difficult. In some circumstances, it may be desirable to remove the filter from the patient's body.

SUMMARY OF THE INVENTION

The present invention relates to retrievable intravascular filter devices and methods for filtering blood clots within a vessel. In an exemplary embodiment of the present invention, a retrievable vena cava filter may comprise a plurality of elongated filter legs each having a hook portion configured to releasably secure the filter to the wall of a vessel, and an expandable member releasably connected to the filter. The filter legs may be biased to expand from a substantially straight configuration to an outswept, conical-shaped configuration when deployed in the vessel. The expandable member may include a plurality of anchoring members configured to pierce and secure the expandable member to the vessel wall. In some embodiments, the expandable member may comprise a bendable member interconnected to several tubular members. In other embodiments, the expandable member may comprise a coiled wire. In use, the expandable member may be utilized to compress the filter legs against the vessel wall.

BRIEF DESCRIPTION OF THE DRAWINGS

FIG. 4 is a perspective view of an intravascular filter device in accordance with another exemplary embodiment of the present invention, wherein the filter device includes an expandable member;

FIG. 5 is a perspective view of the distal portion of one of the filter legs illustrated in FIG. 4;

FIG. 6 is a top view of the intravascular filter device of FIG. 4, showing the filter device engaged within a vessel;

FIG. 7 is a perspective view of an intravascular filter device in accordance with another exemplary embodiment of the present invention, wherein the expandable member comprises a coiled wire;

FIG. 8 is a perspective view of the distal portion of one of the filter legs illustrated in FIG. 7;

FIG. 9 is a partial cross-sectional view of an intravascular filter device temporarily placed in a vessel;

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
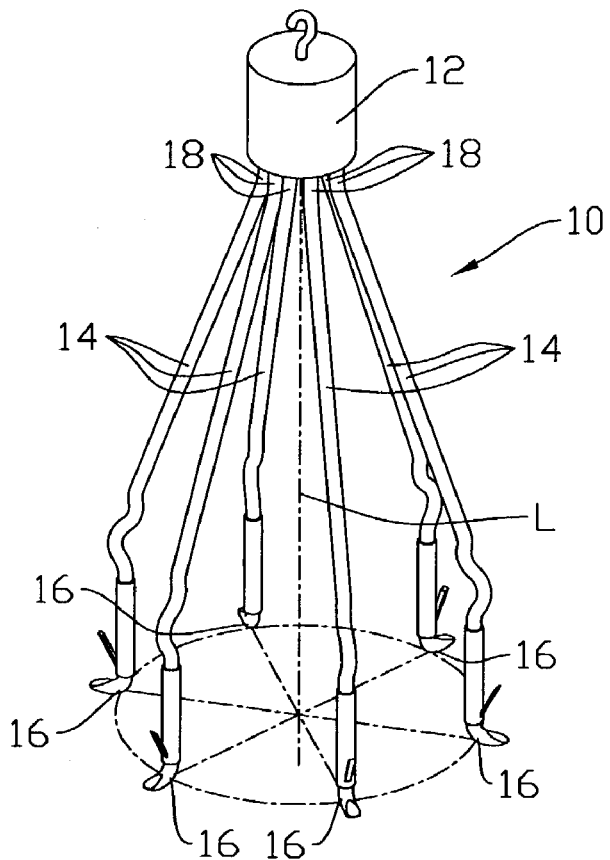
FIG. 1 is a perspective view of an intravascular filter device in accordance with an exemplary embodiment of the present invention.

FIG. 1 is a perspective view of an intravascular filter device 10 in accordance with an exemplary embodiment of the present invention. Intravascular filter 10 comprises an apical head 12, and a plurality of elongated filter legs 14 each having a distal section 16 and a proximal section 18. Each of the filter legs 14 may be configured identically with respect to each other, and may be symmetrically spaced about a central longitudinal axis L in a generally conical-shaped configuration when expanded. The elongated legs 14 may be collectively arranged about the longitudinal axis L such that the proximal section 18 of each filter leg 14 converges at the apical head 12 to form an apex. The filter legs 14 may be biased to expand from a substantially straight position when radially constrained within a delivery device to an outswept position when deployed in a blood vessel.

The filter legs 14 may be formed from a metal such as platinum, gold, tantalum, tungsten, titanium, or a metal alloy such as stainless steel (e.g. type 304V), Beta III Titanium, cobalt-chrome alloy, Elgiloy, L605, MP35N, Ta-10W, 17-4PH, or Aeromet 100. The filter legs 14 may also include an anti-thrombogenic coating such as herapin (or its derivatives), urokinase, or PPack (dextrophenylalanine proline arginine chloromethylketone) to prevent insertion site thrombosis.

In certain embodiments, the filter legs 14 may be formed from a shape-memory material such as nickel-titanium alloy (Nitinol). A slight outward bend can be imparted to each filter leg 14 by heating the alloy beyond its final austenitic temperature, and then bending each filter leg 14 to a pre-defined shape. The filter legs 14 can be configured to revert to their pre-defined (i.e. bent) shape at or near body temperature (37° C.), allowing each individual leg 14 to maintain a straight position until deployed in the vessel.

Figure 2:
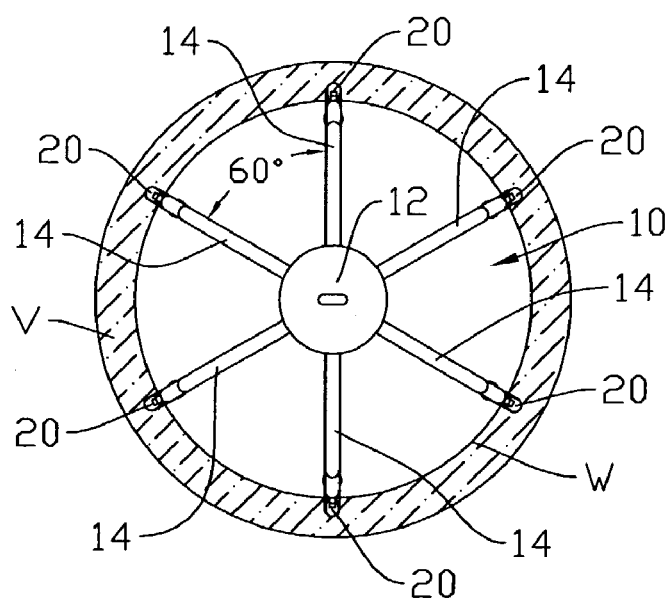
FIG. 2 is a top view of the intravascular filter device of FIG. 1, showing the filter engaged within a vessel.

FIG. 2 is a top view of the intravascular filter device 10 of FIG. 1, showing the filter device 10 deployed within a vessel V. As shown in FIG. 2, the filter legs 14 extend outwardly from the apical head 12 to anchor the filter device 10 along the inner wall W of the vessel V. The filter legs 14 can be arranged at equidistant intervals such that the filter legs 14 are symmetrically spaced about the longitudinal axis formed by the apical head 12. In the exemplary embodiment illustrated, intravascular filter 10 includes six filter legs 14 arranged at 60° intervals. It is to be understood, however, that any number or arrangement of filter legs can be employed in accordance with the present invention.

The distal section 16 of each filter leg 14 includes a hook portion 20 configured to pierce the inner wall of the vessel V and prevent migration of the filter device 10 within the body. In use, each hook portion 20 compresses against the inner wall W of the vessel V as a result of the outwardly directed force exerted by the filter legs 14. The dimensions and material composition of the filter legs 14 can be selected to impart a desired amount of force to the hook portion 20.

Figure 3:
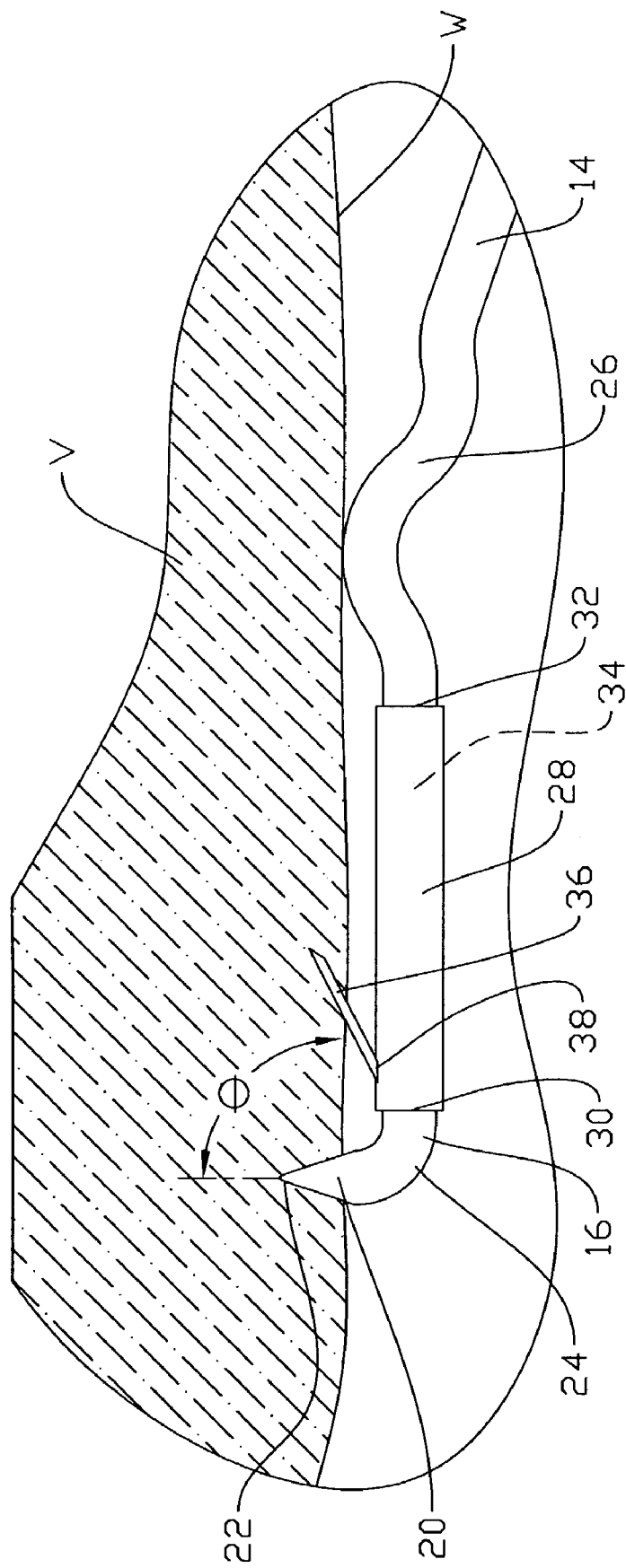
FIG. 3 is a partial perspective view of one of the elongated filter legs illustrated in FIG. 1, showing the filter leg engaged along the wall of the vessel.

FIG. 3 is a perspective view of one of the filter legs 14 illustrated in FIG. 1, showing the filter leg 14 engaged within the wall W of a vessel V. Hook portion 20 includes a sharp tip 22 that pierces the vessel wall W, enabling ligation of the filter within the vessel. In certain embodiments, the hook portion 20 may including a bend region 24 orienting the sharp tip 22 at an angle θ relative to the wall W of the vessel. V. In some embodiments, the bend region 24 orients the hook portion 20 at an angle θ substantially perpendicular to the vessel wall W. In other embodiments, the bend region 24 orients the sharp tip 22 at an acute or obtuse angle θ relative to the vessel wall W. Each of the bend regions 24 can be similarly oriented such that each of the sharp tips 22 pierces the vessel wall W at approximately the same angle.

Intravascular filter device 10 may further include a plurality of tubular members 28 configured to permanently engage the vessel wall W. Each tubular member 28 includes a distal end 30, a proximal end 32, and an inner lumen 34 therebetween configured to slidably receive one of the filter legs 14. A zigzag section 26 on each filter leg 14 prevents the tubular members 28 from retracting proximally toward the proximal section 18, and prevents the conical-shaped filtering portion of each leg 14 from contacting the vessel wall W.

The tubular members 28 may be formed of short segments of hypodermic tubing comprising a metal, metal alloy, or metal-polymer blend. Examples of suitable materials include stainless steel (e.g. type 304V), platinum, tungsten, nickel-titanium alloy, polyethylene terapthalate (PET), polytetraflouroethylene (PTFE), polyurethane (nylon) fluorinated ethylene propylene (FEP), polyurethane, polypropylene (PP), polyvinylchloride (PVC), polyether-ester, polyester, polyamide, elastomeric polyamides, block polyamide/ethers, polyether block amide (PEBA), silicones, polyethylene, polyether-ether ketone (PEEK), polyimide (PI), and polyetherimide (PEI). The inner lumen 34 of each tubular member 28 may also include a lubricious coating such as polytetraflouroethylene (PTFE).

Each tubular member 28 may include a hook, pin, needle, prong, barb, wedge or other piercing means 36 adapted to permanently engage and secure the tubular member 28 to the vessel wall W. The piercing means 36 may be adapted to bend or flex about a joint 38, allowing the piercing means 36 to bend and compress against the tubular member 28 when placed in a delivery catheter or sheath. An anti-inflammatory agent such as dexamethasone, prednisolone, corticosterone, budesonide, estrogen, sulfasalazine, mesalamine, or any suitable combination or mixture thereof may be applied to each filter leg 14 and tubular member 28 to prevent inflammation caused by the engagement of the device along the vessel wall W.

FIG. 4 is a perspective view of an intravascular filter device 110 in accordance with another exemplary embodiment of the present invention, wherein the filter 110 includes an expandable member 140. Intravascular filter device 110 comprises an apical head 112, and a plurality of elongated filter legs 114 each having a distal section 116, a proximal section 118, and a zigzag section 226. As with the previous embodiment, the filter legs 114 may be symmetrically spaced in a generally conical-shaped configuration, and may be configured identically to each other. The filter legs 114 may be biased to expand from a substantially straight position when radially constrained within a delivery device to an outswept position when deployed in the blood vessel.

The expandable member 140 may comprise a plurality of tubular members 128 interconnected by a bendable member 142 biased to radially expand and compress against the wall of the vessel when deployed. As shown in FIG. 5, each tubular member 128 has a distal end 130, a proximal end 132, and an inner lumen 134 configured to slidably receive one of the filter legs 114. A hook, pin, needle, prong, barb, wedge or other piercing means 136 may be used to permanently engage and secure each tubular member 128 to the wall of the vessel. A flexible joint 138 connecting the piercing means 136 to the tubular member 128 allows the piercing means 136 to bend and compress against the tubular member 128 when loaded into the delivery device.

FIG. 6 is a top view showing the intravascular filter device 110 engaged along the wall W of a vessel V. In an expanded position illustrated in FIG. 6, the filter legs 114 extend outwardly from the apical head 112, compressing against the wall W of the vessel V. The hook portion 120 on each filter leg 114 pierces the vessel wall W, fixing the location of the filter 110 within the vessel V.

As can be further seen in FIG. 6, the expandable member 140 likewise expands when deployed in the vessel V. In use, the expandable member 140 maintains the filter legs 114 at equidistant intervals (e.g. 60°) to each other, preventing the filter legs 114 from asymmetrically deploying within the vessel V.

FIG. 7 is a perspective view of an intravascular filter device 210 in accordance with another exemplary embodiment of the present invention, wherein the expandable member 240 comprises a coiled wire 250. Intravascular filter 210 is similar to that depicted in other embodiments described herein, comprising an apical head 212, and a plurality of elongated filter legs 214 each having a distal section 216, a proximal section 218, and a zigzag section 226.

The coiled wire 250 may be formed from a wire having several alternating straight sections 252 and coiled sections 254. As with other embodiments described herein, the coiled wire 250 may be biased to radially expand and compress against the wall of the vessel when deployed. As shown in FIG. 8, each coiled section 254 has a distal end 256, a proximal end 258, and an inner lumen 260 configured to slidably receive one of the filter legs 214. A hook, pin, needle, prong, barb, wedge or other piercing means 236 may be used to permanently engage and secure the expandable member 240 to the wall of the vessel. A flexible joint 238 connecting the piercing means 236 to the coiled section 254 allows the piercing means 236 to bend and compress against the coiled section 254 when loaded into the delivery device.

The coiled wire 250 may be formed from a single piece of wire that can be wound at various locations to form the desired number of coiled sections 254. Each coiled section 254 may be formed by wrapping the wire about a mandrel having an outer diameter slightly larger than the outer diameter of the filter legs. Once the coiled sections 254 have been formed, the wire may then be wrapped around a larger mandrel with the coiled wire sections 254 arranged parallel to the longitudinal axis of the mandrel. The wire can then be connected at its ends and heat set, forming the coiled wire 250 depicted in FIG. 7.

Turning now to FIGS. 9-12, methods of retrieving an IVC filter will now be described with respect to filter device 110 described above. To prepare the filter device 110 prior to insertion in the body, the user straightens the hook portion 120 of each filter leg 114 such that the sharp tip 122 is oriented in a direction substantially parallel to the longitudinal axis of the filter leg 114. With the hook portion 120 straightened, the user inserts the distal section 116 of the filter leg 114 into the lumen 134 of the tubular member 128, and slides the tubular member 128 distally along the filter leg 114 until the proximal end 130 is located immediately adjacent the zigzag region 126. Once loaded, the user bends the distal section 116 of the filter leg 114 to the desired angle (e.g. 90°), and loads the filter 110 into a delivery device such as a catheter or sheath.

Once loaded, the delivery device is then percutaneously inserted into the body, and advanced to a desired vessel within the body (e.g. the inferior vena cava). The filter device 110 is then removed from within the delivery device, causing the filter legs 114 and expandable member 140 to deploy and engage the wall W of the vessel V, as shown in FIG. 9. As the filter 110 is deployed, the sharp tip 122 on hook portion 120 pierces the cava wall W, temporarily fixing the filter 110 within the vessel V. Moreover, the piercing means 136 on each tubular member 128 similarly pierces the cava wall W, fixing the expandable member 140 within the vessel V. With the filter 110 deployed and engaged within the vessel V, embolic debris contained within the blood can then be collected and stored on the filter legs 114.

Figure 10:
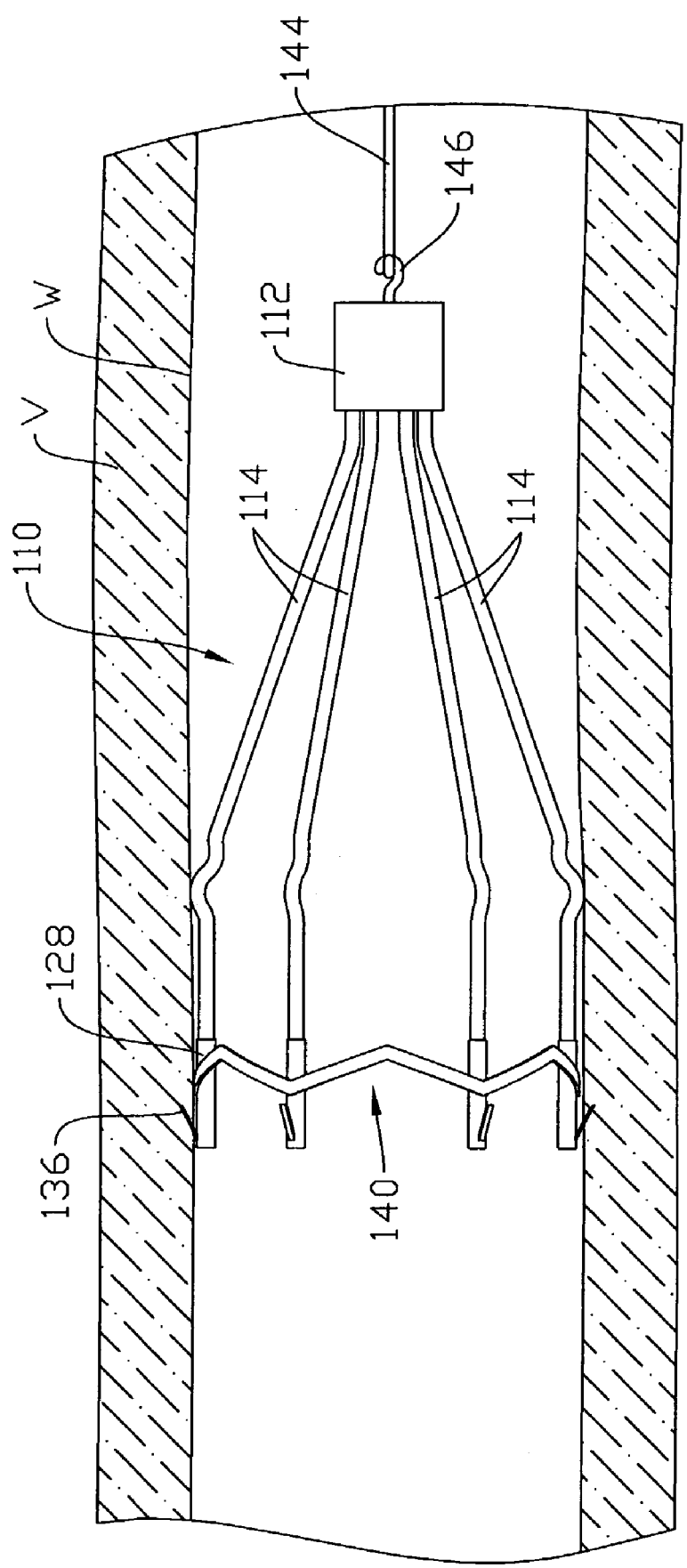
FIG. 10 is another partial cross-sectional view showing the intravascular filter device withdrawn such that the proximal portion of each filter leg is disengaged from the vessel wall.
Figure 11:
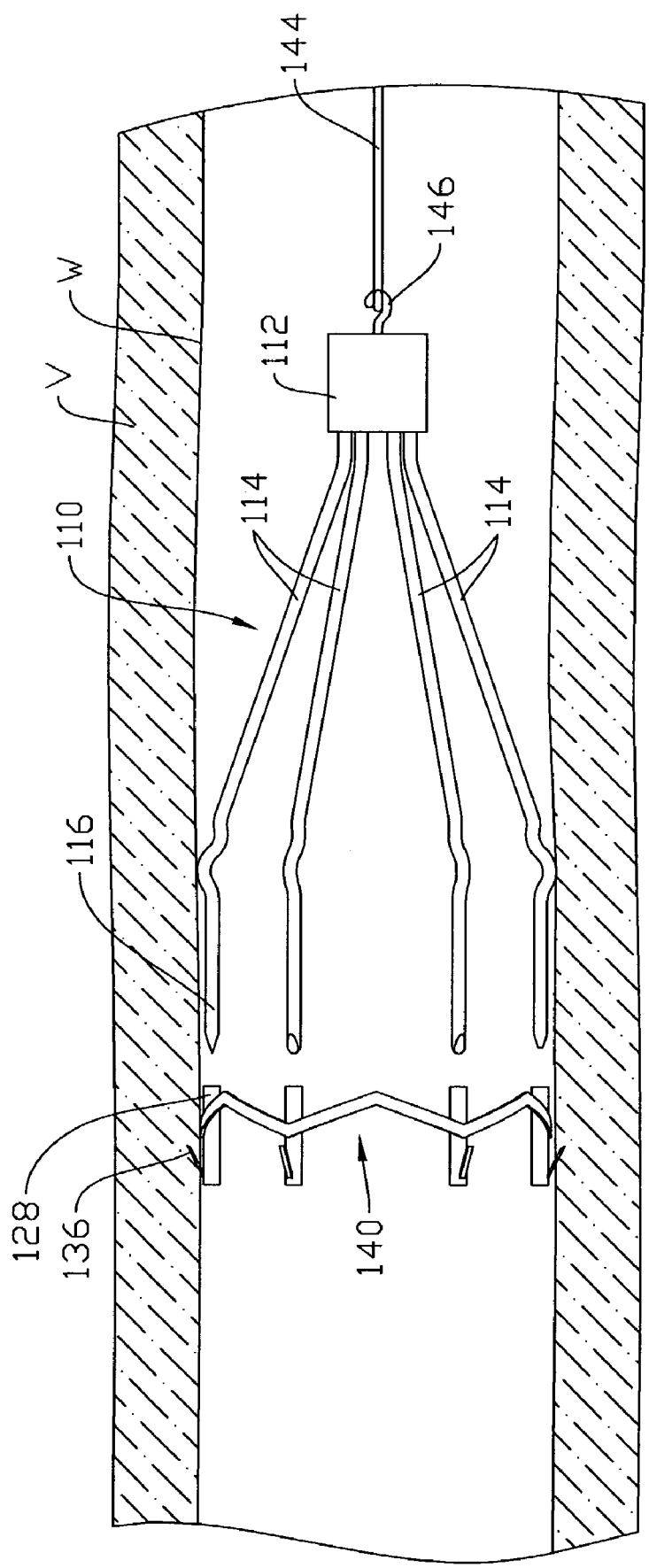
FIG. 11 is another partial cross-sectional view showing the intravascular filter device further withdrawn such that the distal portion of each filter leg is decoupled from the tubular members.
Figure 12:
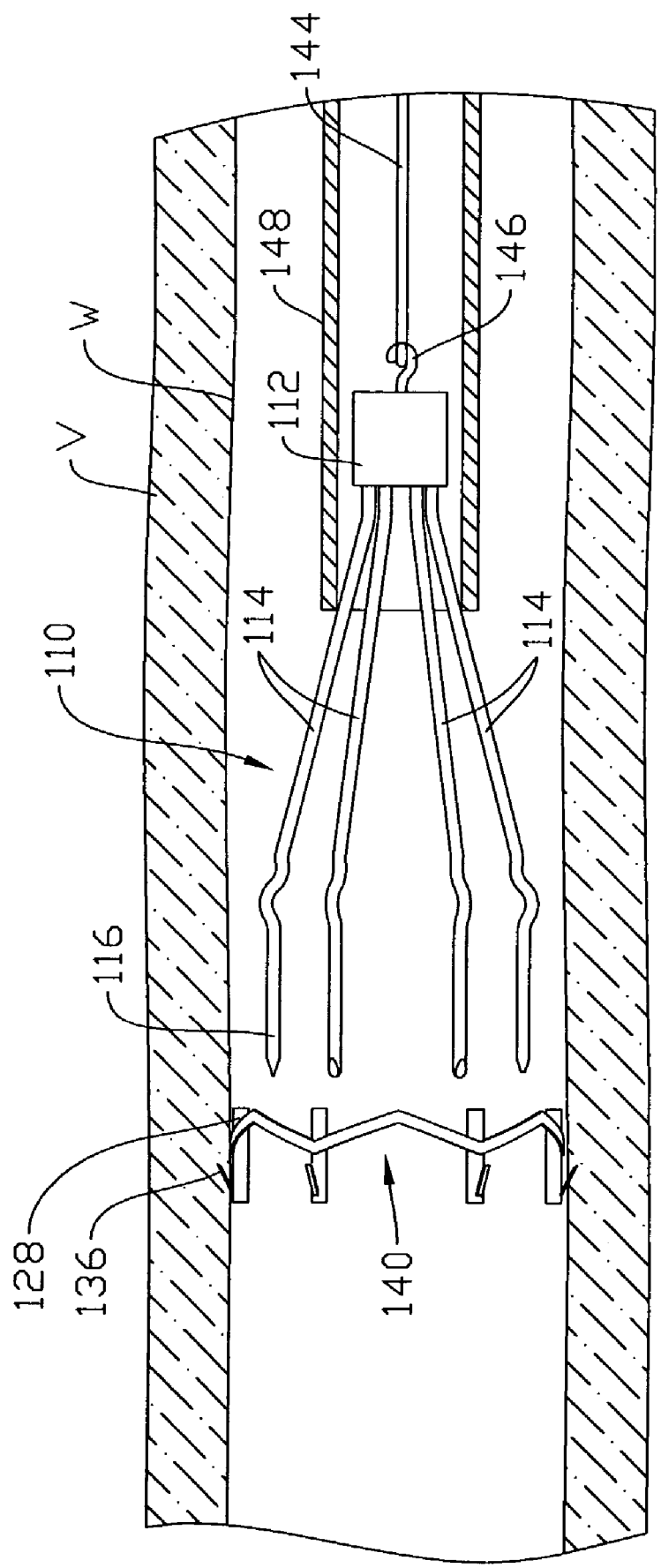
FIG. 12 is another partial cross-sectional view showing the intravascular filter device collapsed at least in part within a retrieval sheath.

To remove the filter device 110 from the vessel, a retrieval mechanism 144 can be utilized to engage a hook 146 on the apical head 112 to retract the filter device 110 proximally a short distance, causing the hook portion 120 on each filter leg 114 to straighten and eject from within the tubular member 128, as shown in FIG. 10. Further retraction of the filter device 110 proximally causes the filter legs 114 to decouple from the expandable member 140, as shown in FIG. 11. A retrieval device such as the sheath 148 depicted in FIG. 12 can then be utilized to radially collapse and remove the filter device 110 from the body.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A retrievable vena cava filter, comprising:
   a plurality of elongated filter legs each having a proximal section and a distal section; and
   an expandable member releasably connected to the filter legs, the expandable member including a plurality of anchor members;
   wherein said expandable member comprises a bendable member and a plurality of tubular members.

2. The retrievable vena cava filter of claim 1, wherein said plurality of elongated filter legs are configured to expand from a substantially straight position to an outswept position when placed in the blood vessel.

3. The retrievable vena cava filter of claim 1, wherein said plurality of elongated filter legs comprise stainless steel.

4. The retrievable vena cava filter of claim 1, wherein said plurality of elongated filter legs comprise a shape-memory material.

5. The retrievable vena cava filter of claim 4, wherein said shape-memory material is nickel-titanium alloy.

6. The retrievable vena cava filter of claim 1, wherein each of said plurality of elongated filter legs includes a bend region.

7. The retrievable vena cava filter of claim 1, wherein each of said elongated filter legs includes a hook portion having a sharp tip.

8. The retrievable vena cava filter of claim 7, wherein said sharp tip is bent at an angle relative to the vessel wall.

9. The retrievable vena cava filter of claim 7, wherein said sharp tip is bent at an angle perpendicular to the vessel wall.

10. The retrievable vena cava filter of claim 1, wherein said expandable member is biased to expand when placed in the blood vessel.

11. The retrievable vena cava filter of claim 1, wherein each of said anchor members includes piercing means for securing the expandable member to the vessel wall.

12. The retrievable vena cava filter of claim 1, further comprising an apical head secured to the proximal section of said plurality of elongated filter legs.

13. The retrievable vena cava filter of claim 1, wherein each of said plurality of elongated filter legs includes a zigzag section.

14. A retrievable vena cava filter, comprising:
   an apical head;
   a plurality of elongated filter legs each having a proximal section and a distal section, the proximal section of said plurality of elongated filter legs being secured to the apical head, the distal section of said plurality of elongated filter legs including a hook portion configured to releasably secure the vena cava filter to the wall of a blood vessel; and
   an expandable member comprising a bendable member and a plurality of tubular members each having an inner lumen configured to slidably receive one of the elongated filter legs, and including piercing means for securing the tubular member to the vessel wall.

* * * * *